US00PP08783P

United States Patent [19]

VandenBerg

[11] Patent Number: Plant 8,783

[45] Date of Patent: Jun. 14, 1994

[54] CHRYSANTHEMUM PLANT NAMED CARMEN

[75] Inventor: Cornelis P. VandenBerg, Salinas, Calif.

[73] Assignee: Yoder Brothers, Inc., Barberton, Ohio

[21] Appl. No.: 61,066

[22] Filed: May 14, 1993

[51] Int. Cl.[5] ..... A01H 5/00

[52] U.S. Cl. ..... Plt./77

[58] Field of Search ..... Plt. 77

*Primary Examiner*—Howard J. Locker

*Attorney, Agent, or Firm*—Foley & Lardner

[57] ABSTRACT

A Chrysanthemum plant named Carmen particularly characterized by its flat capitulum form; decorative capitulum type; white ray floret color with a green overcast in the center of the flower; diameter across face of capitulum of 64 to 79 mm when fully opened, when grown as a single stem spray cut mum; flowering response in Salinas under normal temperatures is 46 to 52 days after start of short days; flowering response in Bogota, Colombia under temperatures of minimum 6.3 degrees Celsius night and maximum 29 degrees Celsius day is 60 to 67 days; plant height is 84 to 107 cm when grown in Salinas with 11 to 13 long days prior to start of short days; height is 117 to 122 cm when grown in Bogota with 14 to 15 long days prior to start of short days; peduncle length of the first lateral at flowering after removing the apical bud without growth regulator applications is 5 to 10 cm when grown in Salinas, and 13 to 15 cm when grown in Bogota; peduncle length of the fourth lateral at flowering is 8 to 15 cm when grown in Salinas, and 18 to 23 cm when grown in Bogota; and excellent tolerance to low night temperatures for bud initiation and flower development.

3 Drawing Sheets

The present invention comprises a new and distinct cultivar of Chrysanthemum, botanically known as *Dendranthema grandifloa,* and referred to by the cultivar name Carmen.

Carmen, identified as 0883 (90-968001), was originated from a cross made by Cornelis P. VandenBerg in a controlled breeding program in Salinas, Calif., in 1990.

The female parent of Carmen was an unnamed seedling, identified as 1123 (85-247002), and described as a flat decorative cut spray mum with a white ray floret color; a diameter of capitulum of 70 to 76 mm; a flowering response in Salinas, Calif. of 47 to 53 days, and in Bogota, Colombia of 60 to 67 days; a plant height in Salinas, Calif. of 74 to 89 cm when grown with 6 to 8 long days prior to start of short days, and of 102 to 122 cm when grown in Bogota, Colombia with 14 to 15 long days prior to start of short days; a peduncle length of the 1st lateral of 10 to 13 cm and of the 4th lateral of 13 to 23 cm, when grown in Salinas, Calif.; a peduncle length of the 1st and the 4th lateral of 10 to 18 cm and 13 to 23 cm when grown in Bogota; a terminal spray formation; and an excellent tolerance to low night temperatures for bud initiation and flower development. The female parent was discarded from all programs on Oct. 16, 1991.

The male parent of Carmen was an unnamed seedling, identified as 1007 (85-245001), and described as a light pink flat decorative spray cut mum with many disc florets; flowering response to short days of 53 to 60 days in Salinas, Calif., and of 70 to 75 days in Bogota, Colombia; a plant height of 86 to 102 cm with 6 to 14 long days prior to start of short days when grown in Salinas, and of 102 to 130 cm with 14 to 17 long days prior to start of short days when grown in Bogota; a peduncle length of the 1st lateral of 8 to 15 cm and of the 4th lateral of 10 to 23 cm, when grown in Salinas, Calif.; a peduncle length of the 1st and the 4th lateral of 8 to 18 cm and 15 to 23 cm when grown in Bogota; a terminal spray formation; and an excellent tolerance to low night temperatures for bud initiation and flower development. The male parent was discarded from all programs on Dec. 7, 1990.

Carmen was discovered and selected as one flowering plant within the progeny of the stated cross by Cornelis P. VandenBerg in February 1991, in a controlled environment in Salinas, Calif.

The first act of asexual reproduction of Carmen was accomplished when vegetative cuttings were taken from the initial selection in May 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Carmen are firmly fixed and are retained through successive generations of asexual reproduction.

Carmen has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside the greenhouse during our trials ranging as low as 6.3 to 10.0 degrees Celsius.

The following traits have ben repeatedly observed and are determined to be basic characteristics of Carmen, which, in combination, distinguish this Chrysanthemum as a new and distinct cultivar:

1. Flat capitulum form.
2. Decorative capitulum type.
3. White ray floret color with a green overcast in the center of the flower.

4. Diameter across face of capitulum of 64 to 79 mm when fully opened, when grown as a single stem spray cut mum.

5. Flowering response in Salinas under normal temperatures is 46 to 52 days after start of short days. Flowering response in Bogota, Colombia under temperatures of minimum 6.3 degrees Celsius night and maximum 29 degrees Celsius day is 60 to 67 days.

6. Plant height is 84 to 107 cm when grown in Salinas with 11 to 13 long days prior to start of short days; height is 117 to 122 cm when grown in Bogota with 14 to 15 long days prior to start of short days.

7. Peduncle length of the first lateral at flowering after removing the apical bud without growth regulator applications is 5 to 10 cm when grown in Salinas, and 13 to 15 cm when grown in Bogota. Peduncle length of the fourth lateral at flowering is 8 to 15 cm when grown in Salinas, and 18 to 23 cm when grown in Bogota.

8. Excellent tolerance to low night temperatures for bud initiation and flower development.

The accompanying photographic drawings show typical inflorescence and leaf characteristics of Carmen, with the colors being as nearly true as possible with illustrations of this type.

Sheet 1 is a color photograph of Carmen grown as a single stem spray cut mum.

Sheet 2 is a black and white photograph of three views of the inflorescence of Carmen.

Sheet 3 is a black and white photograph showing the upper and under sides of the leaves of Carmen at 3 stages of development (mature, intermediate and immature). In sheets 2 and 3 a measuring tape in centimeters has been added.

Of the commercial cultivars known to the inventor, the most similar in comparison to Carmen is the cultivar identified as Tayrona, disclosed in Plant Pat. No. 7,482. Reference is made to attached Chart A, which compares certain characteristics of Carmen with the same characteristics of Tayrona.

Similar traits are ray floret color, capitulum form and type, and excellent low night temperature tolerance. Carmen has a slightly larger diameter of capitulum, a faster flowering response, a taller plant height and a shorter peduncle length in Salinas when compared with Tayrona.

In the following description color references are made to The Royal Horticultural Society Colour Chart. The color values were determined on plant material grown as a single stem spray cut mum in Salinas, Calif. on Dec. 15, 1992.

Classification:

*Botanical.*—*Dendranthema grandiflora* cv Carmen.

*Commercial.*—Decorative spray cut mum.

I. INFLORESCENCE

A. Capitulum:

*Form.*—Flat.

*Type.*—Decorative.

*Diameter across face.*—64 to 79 mm when fully opened.

B. Corolla of ray florets:

*Color (general tonality from a distance of three meters).*—White with green center.

*Color (upper surface).*—155D to clear white.

*Color (under surface).*—155D to clear white.

*Shape.*—Straight, oblong, cross section concave.

C. Corolla of disc florets:

*Color (mature).*—14B.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—84 to 107 cm when grown in Salinas with 11 to 13 long days prior to start of short days, and 117 to 122 cm when grown in Bogota with 14 to 15 long days prior to start of short days.

B. Foliage:

*Color (upper surface).*—147A.

*Color (under surface).*—147B.

*Shape.*—See photograph.

CHART A

COMPARISONS MADE OF PLANTS GROWN AS SINGLE STEM SPRAY CUT MUMS IN SALINAS, CALIFORNIA AND IN BOGOTA, COLOMBIA

| CULTIVAR | CARMEN | TAYRONA |
|---|---|---|
| Ray floret color | White with green center | White with green center |
| Capitulum form and type | Flat decorative | Flat decorative |
| Diameter across face of capitulum | 64 to 79 mm | 63 to 73 mm |
| Flowering Response | | |
| in Salinas | 46 to 52 days | 50 to 57 days |
| in Bogota | 60 to 67 days | 64 to 68 days |
| Plant height | | |
| in Salinas | 84 to 107 cm | 74 to 86 cm |
| in Bogota | 117 to 122 cm | 97 to 119 cm |
| Penduncle length: | | |
| 1st lateral Salinas | 5 to 10 cm | 10 to 15 cm |
| 4th lateral Salinas | 8 to 15 cm | 13 to 20 cm |
| 1st lateral Bogota | 13 to 15 cm | 13 to 15 cm |
| 4th lateral Bogota | 18 to 23 cm | 20 to 23 cm |
| Low night temperature tolerance | Excellent | Excellent |

I claim:

1. A new and distinct Chrysanthemum plant named Carmen, as described and illustrated.

* * * * *

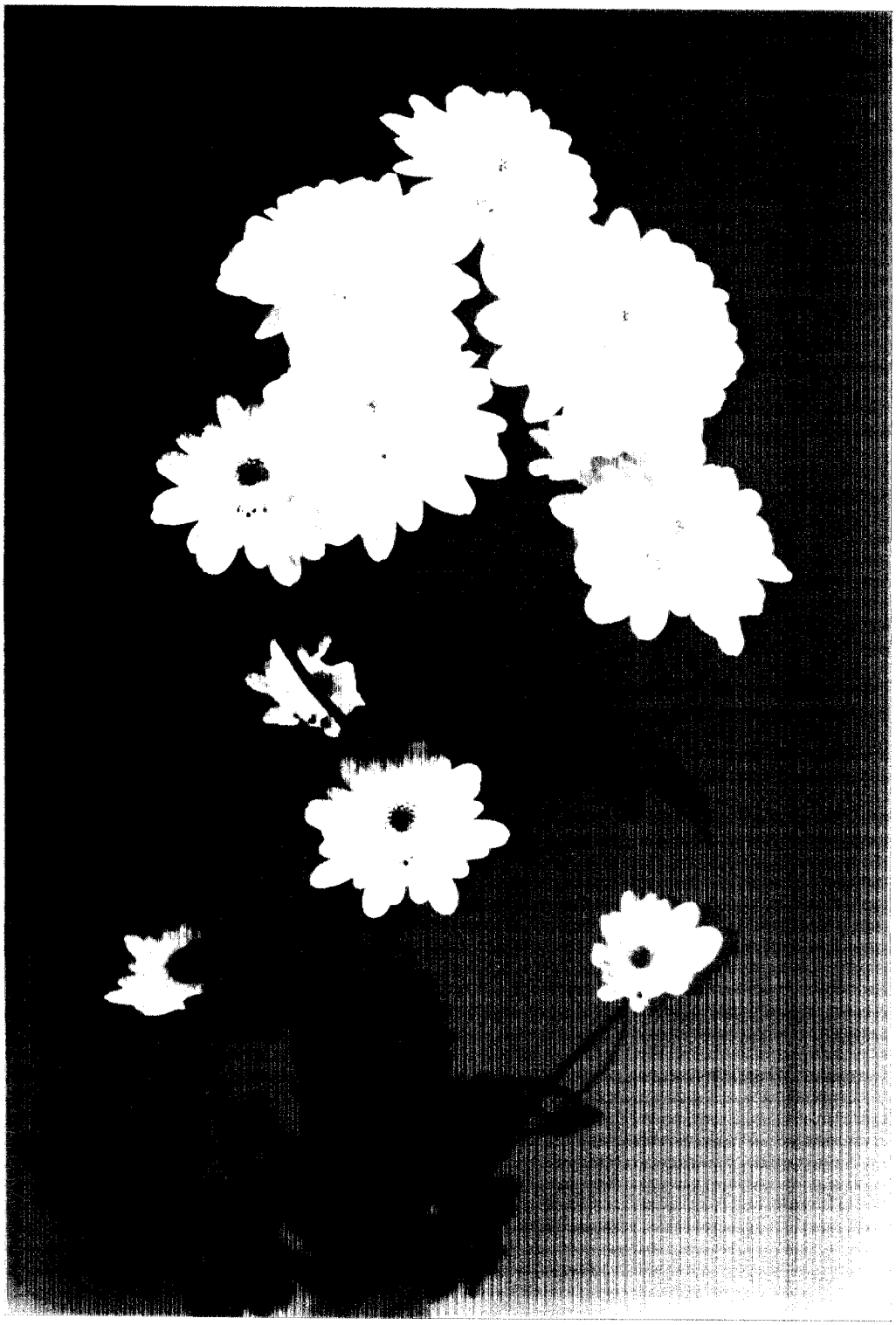

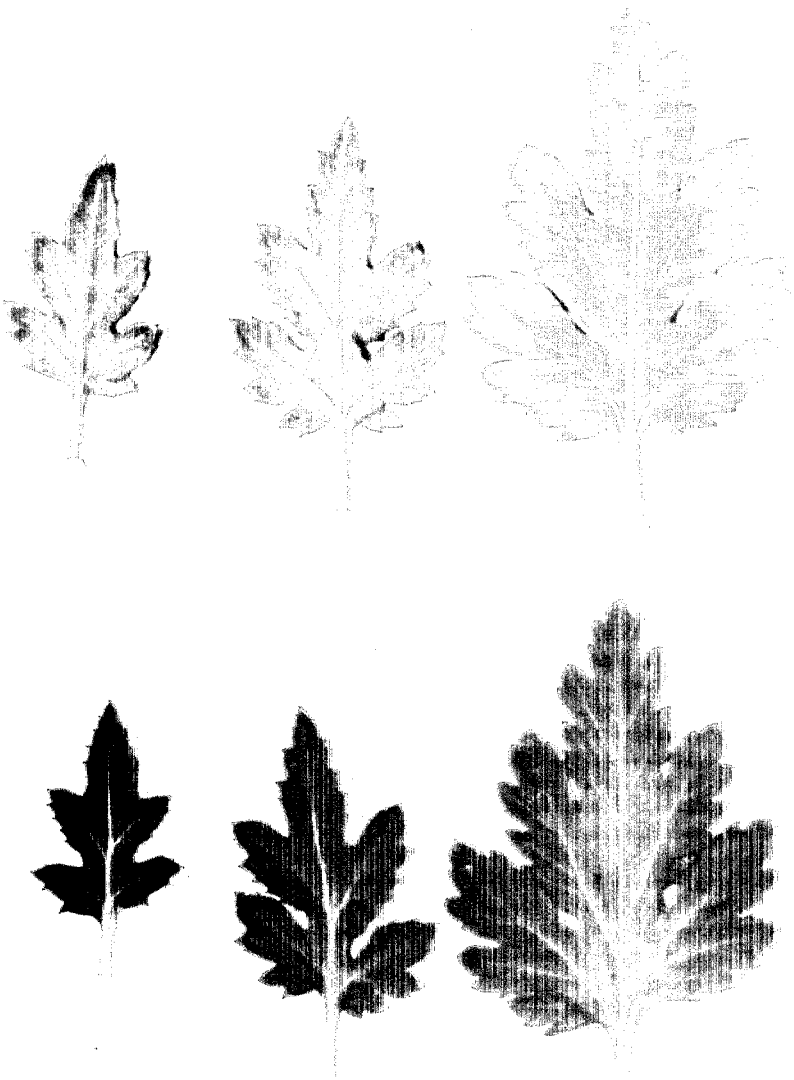

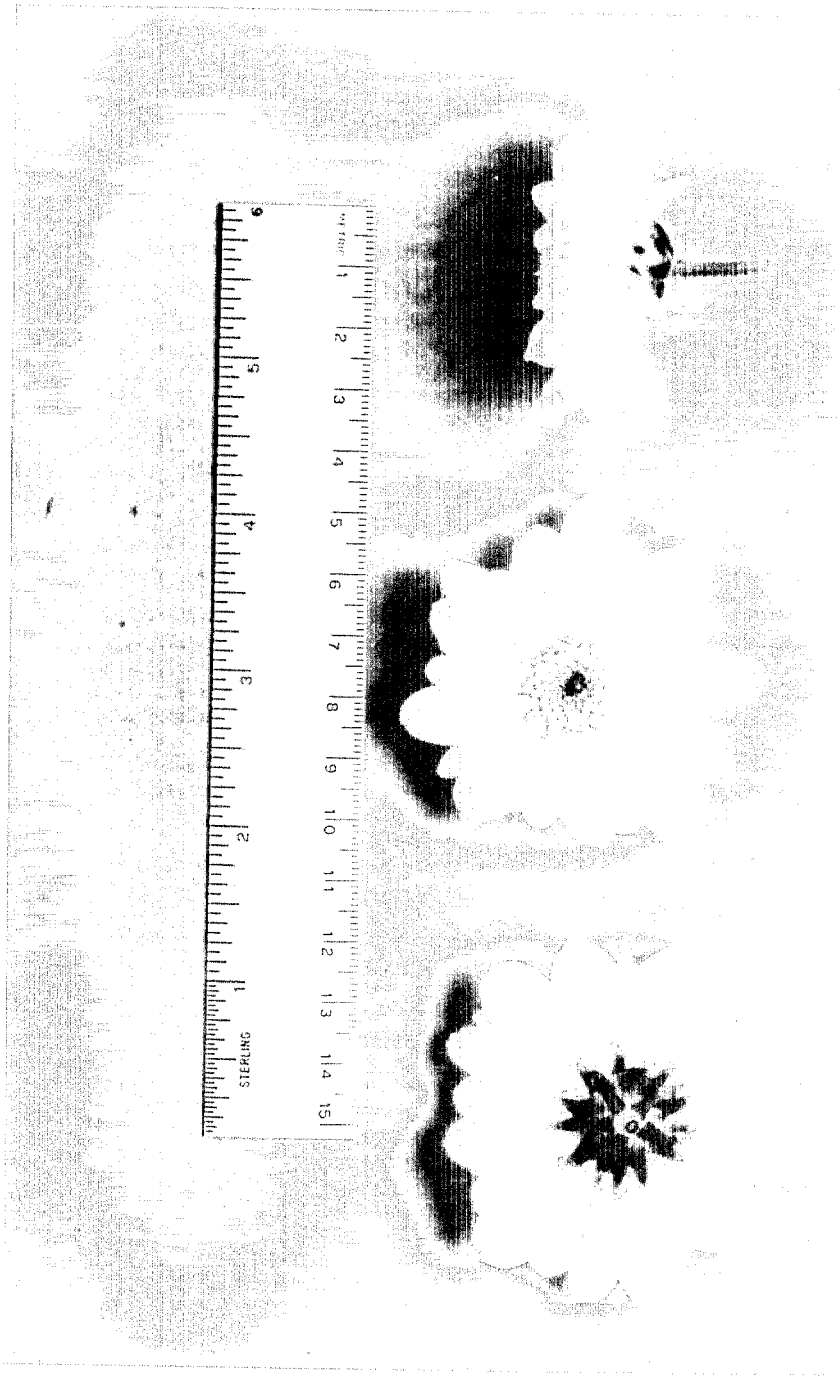
STERLING